United States Patent [19]
Nagai et al.

[11] 3,983,239
[45] Sept. 28, 1976

[54] HEXAHYDRO-γ-CARBOLINE DERIVATIVES AND THEIR SALTS

[75] Inventors: Yasutaka Nagai, Mukou; Hitoshi Uno, Takatsuki; Masanao Shimizu, Kobe; Tadahiko Karasawa, Toyonaka, all of Japan

[73] Assignee: Dainippon Pharmaceutical Co., Ltd., Osaka, Japan

[22] Filed: Mar. 12, 1975

[21] Appl. No.: 557,642

[30] Foreign Application Priority Data
Mar. 20, 1974 Japan.............................. 49-31966

[52] U.S. Cl............................ 424/267; 260/293.55
[51] Int. Cl.²...................................... C07D 471/04
[58] Field of Search................. 260/293.55; 424/267

[56] References Cited
UNITED STATES PATENTS

| | | | |
|---|---|---|---|
| 3,466,293 | 9/1969 | Johnson et al.................. | 260/294.9 |
| 3,657,254 | 4/1972 | Barkov et al. ................. | 260/293.55 |

Primary Examiner—G. Thomas Todd
Attorney, Agent, or Firm—Stevens, Davis, Miller & Mosher

[57] ABSTRACT

Hexahydro-γ-carboline derivatives of the formula:

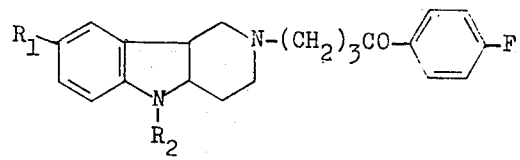

wherein $R_1$ is methyl or ethyl, and $R_2$ is hydrogen, methyl or ethyl, with proviso that when $R_1$ is ethyl, $R_2$ is hydrogen, and their pharmaceutically acceptable acid addition salts, which exhibit excellent psychotropic effect, and a process for the preparation thereof.

16 Claims, No Drawings

HEXAHYDRO-γ-CARBOLINE DERIVATIVES AND THEIR SALTS

The present invention relates to novel and pharmacologically active hexahydro-γ-carboline derivatives and their pharmaceutically acceptable acid addition salts, and a process for the preparation thereof. More particularly, it relates to 8-alkyl-2-[γ-(p-fluorobenzoyl)-propyl]-2,3,4,4a,5,9b-hexahydro-1H-pyrido[4,3-b]indoles of the formula:

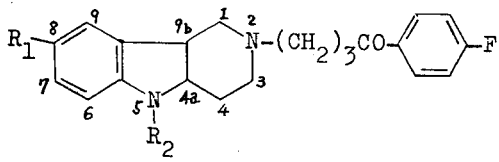

[I]

wherein $R_1$ is methyl or ethyl, and $R_2$ is hydrogen, methyl or ethyl, with proviso that when $R_1$ is ethyl, $R_2$ is hydrogen, and their pharmaceutically acceptable acid addition salts, and a process for the preparation thereof.

The compounds of the formula [I] and their pharmaceutically acceptable acid addition salts show not only central nervous system depressing activities similar to those of the existing neuroleptics (e.g. chlorpromazine or haloperidol) but also a unique pharmacological activity such as potentiating activity of the methamphetamine-induced stereotypy which suggests that the compounds have an antidepressant-like activity. Thus, the compounds of the present invention are expected to be useful as a new type of a neuroleptic which exhibits excellent effect on the autism and abulia or the disturbance of affect which appear in schizophrenia patients.

Hitherto, some compounds having a similar chemical structure to that of the present compounds have been reported. For instance, R. P. Johnson et al have reported that 8-substituted-2-[γ-(p-fluorobenzoyl)-propyl]-2,3,4,5-tetrahydro-1H-pyrido-[4,3-b]indoles are central nervous system depressants with pronounced analgesic activity (R. P. Johnson et al; U.S. Pat. No. 3,466,293 and Arch. Int. Pharmacodyn., Vol. 190, pages 124-134 (1971), etc.). However, these compounds of R. P. Johnson has no potentiation of the methamphetamine-induced stereotypy which is shown by the present compounds.

Moreover, the compounds having the same structure, except the substituent at the 8 position, as the present compounds, such as 8-methoxy, hydrogen or fluoro-2-[γ-(p-fluorobenzoyl)propyl]-2,3,4,4a,5,9b-hexahydro-1H-pyrido[4,3-b]indoles, show merely the central nervous system depressing activities but show no potentiation of the methamphetamine-induced stereotypy.

Besides, it has been reported that 2,8-dimethyl-2,3,4,4a,5,9b-hexahydro-1H-pyrido[4,3-b]indole (i.e. dicarbine), which has a hexahydro-γ-carboline nucleus like the compounds of the present invention, shows an antipsychotic activity and a thymoleptic activity in clinical trials [Psychopharmacologia, Vol. 21, pages 82-88 (1971)]. They say that this compound is a unique drug since it shows both of central nervous system depressing activities similar to those of the existing neuroleptics and as antidepressant-like activity, particularly, it shows the biphasic activities against amphetamine which has the same pharmacological activities as methamphetamine, i.e. it shows an antagonism against amphetamine and also an activity of potentiating the amphetamine-induced stereotypy. However, the central nervous system depressing activities of this known compound are far weak in comparison with those of the present compounds.

An object of the present invention is to provide novel hexahydro-γ-carboline derivatives and their pharmaceutically acceptable acid addition salts having excellent central nervous system depressing activities as well as an activity of potentiating the methamphetamine-induced stereotypy.

Another object of the invention is to provide a unique type of a neuroleptic.

A further object of the invention is to provide a pharmaceutical composition useful for treating schizophrenia, which contains said hexahydro-γ-carboline derivative or its pharmaceutically acceptable acid addition salt as set forth above as the essential active ingredient.

A more further object of the invention is to provide a use of said hexahydro-γ-carboline derivatives and their pharmaceutically acceptable acid addition salts as set forth above as a neuroleptic.

A still further object of the invention is to provide a process for preparing said hexahydro-γ-carboline derivatives and their pharmaceutically acceptable acid addition salts as set forth above and a pharmaceutical composition.

These and other objects will be apparent from the description hereinafter.

The hexahydro-γ-carboline derivatives of the present invention have the chemical formula [I] as shown above. Among these compounds, the most preferred one is 8-methyl-2-[γ-(p-fluorobenzoyl)propyl]-2,3,4,4a,5,9b-hexahydro-1H-pyrido[4,3-b]-indole and its pharmaceutically acceptable acid addition salts.

The excellent pharmacological activities of the present compounds are illustrated by the following experimental tests.

1. Potentiation of methamphetamine-induced stereotypy

This test was carried out by a modified method of R. T. Naylor (Life Sci., Vol. 10, page 909, 1971).

To male Wistar HLA rats, weighing 200 to 250 g (each group: 6 rats), were intraperitoneally administered the compounds to be tested. After 20 minutes, methamphetamine (2 mg/kg) was intraperitoneally administered to the test animals, and then the appeared stereotypy was observed. The effects of the test compounds were evaluated by the intensity of the stereotypy and the termination thereof. The results are shown in the following Table 1.

Table 1

| Test compounds* | Dose (mg/kg) | Stereotypy | |
|---|---|---|---|
| | | Intensity | Termination |
| A | 1.0 | 0 | 0 |
| | 2.0 | ++ | ++ |
| | 5.0 | +++ | +++ |
| | 10.0 | +++ | +++ |
| B | 2.0 | + | + |
| | 5.0 | +++ | +++ |

Table 1-continued

| Test compounds* | Dose (mg/kg) | Stereotypy Intensity | Stereotypy Termination |
|---|---|---|---|
|  | 10.0 | +++ | +++ |
| C | 1.0 | 0 | 0 |
|  | 2.0 | 0 | 0 |
|  | 5.0 | ++ | ++ |
|  | 10.0 | ++ | +++ |
| D | 1.0 | 0 | 0 |
|  | 2.0 | 0 | 0 |
|  | 5.0 | + | ++ |
|  | 10.0 | +++ | +++ |
| Reference** compounds |  |  |  |
| 1 | 1.0 | 0 | 0 |
|  | 2.0 | 0 | 0 |
|  | 5.0 | 0 | 0 |
|  | 10.0 | 0 | 0 |
| 2 | 1.0 | 0 | 0 |
|  | 2.0 | 0 | 0 |
|  | 5.0 | 0 | 0 |
|  | 10.0 | — | 0 |
| 3 | 1.0 | 0 | 0 |
|  | 2.0 | 0 | 0 |
|  | 5.0 | — | — |
|  | 10.0 | — | — |
| 4 | 1.0 | 0 | 0 |
|  | 2.0 | 0 | 0 |
|  | 5.0 | 0 | 0 |
|  | 10.0 | — | 0 |
| 5 | 0.1 | 0 | — |
|  | 0.2 | — | — |
|  | 0.5 | — | — |
|  | 1.0 | — | — |
| 6 | 2.0 | 0 | 0 |
|  | 5.0 | — | + |
|  | 10.0 | — | — |
| 7 | 1.0 | 0 | 0 |
|  | 2.0 | + | ++ |
|  | 5.0 | ++ | +++ |
|  | 10.0 | +++ | +++ |

[Note]:
1. The symbols in Table 1 have the following meanings.
   ———: Marked antagonism
   ——: Moderate antagonism
   —: Slight antagonism
   0: No interaction
   +: Slight potentiation
   ++: Moderate potentiation
   +++: Marked potentiation
2. Test compounds* are as follows:
   A: 8-Methyl-2-[γ-(p-fluorobenzoyl)propyl]-2,3,4,4a,5,9b-hexahydro-1H-pyrido[4,3-b]indole dihydrochloride
   B: 8-Ethyl-2-[γ-(p-fluorobenzoyl)propyl]-2,3,4,4a,5,9b-hexahydro-1H-pyrido[4,3-b]indole dihydrochloride
   C: 5,8-Dimethyl-2-[γ-(p-fluorobenzoyl)propyl]-2,3,4,4a,5,9b-hexahydro-1H-pyrido[4,3-b]indole dihydrochloride
   D: 5-Ethyl-8-methyl-2-[γ-(p-fluorobenzoyl)propyl]-2,3,4,4a,5,9b-hexahydro-1H-pyrido[4,3-b]indole dihydrochloride
3. Reference compounds** are as follows:
   1: 8-Methyl-2-[γ-(p-fluorobenzoyl)propyl]-2,3,4,5-tetrahydro-1H-pyrido[4,3-b]indole hydrochloride (disclosed in U.S. Pat. 3,466,293)
   2: 2-[γ-(p-Fluorobenzoyl)propyl]-2,3,4,4a,5,9b-hexahydro-1H-pyrido[4,3-b]indole dihydrochloride [prepared in a similar manner as described in Examples of the present specification, m.p. 198 – 202°C (decomp)]
   3: 8-Fluoro-2-[γ-(p-fluorobenzoyl)propyl]-2,3,4,4a,5,9b-hexahydro-1H-pyrido[4,3-b]indole dihydrochloride [prepared in a similar manner as described in Examples of the present specification, m.p. 166 – 170°C]
   4: 8-Methoxy-2-[γ-(p-fluorobenzoyl)propyl]-2,3,4,4a,5,9b-hexahydro-1H-pyrido[4,3-b]indole dihydrochloride [prepared in a similar manner as described in Examples of the present specification, m.p. 213 – 216°C]
   5: Haloperidol
   6: Chlorpromazine
   7: Dicarbine As shown in Table 1, the compounds of the present invention showed a potentiating effect as potent as dicarbine on the methamphetamine-induced stereotypy at 2–10 mg/kg i.p. in rats.

In addition, the compounds of the present invention possess the actions enhancing the apomorphine-induced gnawing and activating the electroencephalogram (EEG), which are suggestive of a property of activating the central nervous system. For example, in rats, the compound A at 0.03–0.7 mg/kg s.c. increased the incidence of gnawing after the administration of apomorphine. And, in gallamine immobilized cats, the compound A at 5 mg/kg i.v. caused a change in the spontaneous EEG to the activating patterns characterized by a low-voltage high frequency in the cortex and a prolongation of arousal time in the hippocampus.

2. Depression of the central nervous system

The compounds of the present invention show the same central nervous system depressing pattern as the existing neuroleptics, such as an inhibiting activity of locomotion, an inhibiting activity of conditioned avoidance response, a cataleptogenic activity, a muscle relaxant activity, an inhibiting activity of self-stimulation, and an anti-methamphetamine activity in terms of locomotor activity.

For instance, these activities of 8-methyl-2-[γ-(p-fluorobenzoyl)propyl]-2,3,4,4a,5,9b-hexahydro-1H-pyrido-[4,3-b]indole dihydrochloride [Compound A in the above Test (1)] are shown in the following Table 2.

Table 2

| Item | Animal | Route | ED$_{50}$ value (mg/kg) Compound A | Dicarbine | Chlorpromazine | Clozapine 1) | Test Method |
|---|---|---|---|---|---|---|---|
| Inhibiting activity of locomotion | mice | p.o. | 9.30 | 149.8 | 6.34 | 7.50 | 2) |
|  | rats | p.o. | 33.2 | >200 | 9.88 | 27.4 | 3) |
|  |  | i.p. | 2.80 | 28.7 | 2.41 | 5.54 |  |
| Inhibiting activity of conditioned avoidance response | mice | p.o. | 10.0 | 119.0 | 5.65 | 9.75 | 4) |
|  | rats | p.o. | 23.8 | >100 | 7.04 | 34.7 | 5) |
| Cataleptogenic activity | rats | p.o. | 34.0 | >100 | 16.1 | >100 | 6) |
| Muscle relaxant activity | rats | p.o. | 11.2 | >100 | 4.38 | 28.1 | 7) |
|  |  | i.p. | 3.16 | 60.3 | 2.07 | 5.41 |  |
| Inhibiting activity of self-stimulation | rats | p.o. | 61.8 | >100 | 7.04 | 61.8 | 8) |

[Note]:
1) Clozapine is a neuroleptic which has been used in Switzerland etc. and the chemical name thereof is 8-chloro-11-(4-methyl-1-piperazinyl)-5H-dibenzo[b,e][1,4]-diazepine.

Table 2-continued

2) Animex method
3) Open-field method [C.S. Hall; J. Comp. Physiol. Psychol. Vol. 18, page 385 (1934)]
4) M.E. Jarvik et al; Psychol. Rep., Vol. 21, page 221 (1967)
5) Shuttle box method [R. Ader et al; J. Pharmacol. Exp. Ther., Vol. 121, page 144 (1957)]
6) P. Muller et al; J. Pharm. Pharmacol., Vol. 26, page 981 (1974)
7) S. Courvoisier et al; "Psychotropic Drugs" (ed. S. Garrattini et al), Elsevier Publishing Company, 1957, page 373
8) J. Olds et al; J. Comp. Physiol. Psychol., Vol. 47, page 419 (1954)

As shown in Table 2, the compound A of the present invention showed excellent central nervous system depressing activities, which were somewhat inferior to those of chlorpromazine, but were almost comparable to those of clozapine and far superior to those of dicarbine.

3. Effect on homovanillic acid (HVA for short) in brain

This test was carried out by a modified method of T. Karasawa et al. [Life Sci., Vol. 15, page 1465 (1974)].

To male Wistar rats, weighing 160 to 200 g (each group: 5 rats), was administered 8-methyl-2-[γ-(p-fluorobenzoyl)propyl]-2,3,4,4a,5,9b-hexahydro-1H-pyrido[4,3-b]indole dihydrochloride (Compound A) intraperitoneally or orally. After 90 minutes in case of the intraperitoneal administration, or after 6 hours in case of the oral administration, the test animals were decapitated, and then the HVA in the brain was measured by a fluorometric method.

As the results, the Compound A, like the existing neuroleptics, remarkably increased the HVA in the brain by the intraperitoneal administration of 5 mg/kg or larger and by the oral administration of 13 mg/kg or larger.

4. Toxicity
a. Acute toxicity

Male and female STD-dd Y mice, weighing 20 to 22 g (each group: 10 mice) and male Wistar HLA rats, weighing 250 to 300 g (each group: 10 to 20 rats) were used. After administering the test compounds, the animals were observed for 7 days, and then the $LD_{50}$ value was calculated by a probit method. The results are shown in the following Table 3.

Table 3

| Animal | Route | Sex | $LD_{50}$ value (mg/kg) ||||
| | | | Compound A | Dicarbine | Chlorpromazine | Clozapine* |
|---|---|---|---|---|---|---|
| Mice | p.o. | male | 589 | 357 | 476 | 202 |
| | | female | 339 | — | — | 212 |
| | i.p. | male | 134 | 153 | — | — |
| | | female | 95 | — | — | — |
| | s.c. | male | 373 | 237 | — | 194 |
| | i.v. | male | 59 | 79 | — | 37 |
| Rats | p.o. | male | 812 | — | — | 251 |
| | i.p. | male | 146 | — | — | — |
| | s.c. | male | 592 | — | — | 272 |
| | i.v. | male | 51 | — | — | 42 |

[Note]: *) The animals were observed for 4 days.

(b) Subacute toxicity

To male JCL-SD rats of 7 week age, weighing about 200 g (each group: 10 rats), was repeatedly administered 8-methyl-2-[γ-(p-fluorobenzoyl)propyl]-2,3,4,4a,5,9b-hexahydro-1H-pyrido[4,3-b]indole dihydrochloride (Compound A) in doses of 10, 30, 100 and 300 mg/kg/day through oral route for 1 month.

As the results, with respect to the weight gain and the food intake, there was no difference between the groups, to which Compound A was administered in doses of 10 to 100 mg/kg/day, and the control group, to which no Compound A was administered, but in the group administered with the Compound A in a dose of 300 mg/kg/day, there was observed a remarkable decrease thereof and some animals were died. On the other hand, with respect to the protein in urine, there was observed no significant change in all groups.

Thus, the compounds [I] and their pharmaceutically acceptable acid addition salts of the present invention have excellent psychotropic effects and low toxicity, and are useful as a neuroleptic.

The compounds of the present invention may be administered alone, but are preferably used in admixture with pharmaceutically acceptable carriers. The compounds may be administered through oral route or parenteral route, but is preferably administered through oral route.

The compounds of the present invention may be used in a form of pharmaceutical compositions, such as tablets, capsules, granules, powders, syrups, suppositories or injections, which can be prepared by a conventional method using inorganic or organic, solid or liquid pharmaceutically acceptable excipients which are suitable for enteral or parenteral administration. The pharmaceutically acceptable excipients are the substances which are unreactive with the present compounds, and may be, for instance, water, gelatin, lactose, starch, cellulose, preferably microcrystalline cellulose, sodium carboxymethyl cellulose, calcium carboxymethyl cellulose and methyl cellulose, sorbitol, light anhydrous silicic acid, magnesium stearate, talc, vegetable fats or oils, hardened oil, benzyl alcohol, gums, propylene glycol, polyalkylene glycols or methylparaben.

The dosage of the present compounds will depend on the body weight, age and conditions of the patients and the chosen route of the administration, or the like, but they may usually be administered in a dose of 25 to 1,800 mg/day, preferably 50 to 300 mg/day, through oral route in adults. The total dosage may be administered once a day or in smaller portions two, three or four times daily, as determined by the attending physician.

The compounds [I] and their pharmaceutically acceptable acid addition salts of the present invention may be prepared by anyone of the following processes (1) to (5).

Process (1):

They may be prepared by reacting a compound of the formula:

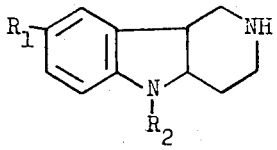

[II]

wherein $R_1$ and $R_2$ are as defined in the first instance, or its salt with a compound of the formula:

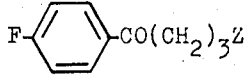

[III]

wherein Z is a residue of reactive ester of alcohol.

The residue of reactive ester of alcohol as defined for Z includes a halogen (e.g. chlorine, bromine or iodine), an arylsulfonyloxy (e.g. p-toluenesulfonyloxy, or benzenesulfonyloxy) or an alkylsulfonyloxy (e.g. methanesulfonyloxy).

The reaction of the Process (1) may be carried out by heating a mixture of the compound [II] and an equimolar or slightly excess amount of the compound [III] in the presence or absence of an inert solvent, such as an aromatic hydrocarbon (e.g. benzene, toluene or xylene), a lower alkanol (e.g. aqueous or anhydrous ethanol, isopropanol or n-butanol), a lower alkanone (e.g. acetone, methyl ethyl ketone or 4-methyl-2-pentanone), a halogenated hydrocarbon (e.g. ethylene chloride), dimethylformamide, or dimethylsulfoxide. Suitable reaction temperature may be 70° to 160°C.

The reaction may optionally be carried out in the presence of a basic condensing agents, such as an alkali metal carbonate (e.g. potassium carbonate or sodium carbonate), an alkali metal hydrogen carbonate (e.g. potassium hydrogen carbonate or sodium hydrogen carbonate), or a tertiary amine (e.g. triethylamine). The reaction may proceed more smoothly by adding thereto an alkali metal iodide (e.g. sodium iodide or potassium iodide).

Besides, the keto group included in the compound [III] may be optionally protected by a suitable protecting group, such as a ketal (e.g. ethylene ketal). When the obtained compound [I] includes such a protecting group in the molecule, it is usually treated with an acid to remove the protecting group.

The starting material [II] in the above Process (1) may be prepared, for example, by the following processes.

The compound [II] wherein $R_2$ is hydrogen may be prepared by reducing a compound of the formula:

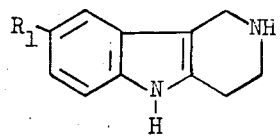

[IV]

wherein $R_1$ is as defined in the first instance, which is prepared in a similar manner as described in U.S. Pat. No. 3,466,293 by catalytic hydrogenation in a dilute borofluoric acid in the presence of platinum.

The compound [II] wherein $R_1$ is methyl and $R_2$ is methyl or ethyl may be prepared by reacting the compound [II] wherein $R_1$ is methyl and $R_2$ is hydrogen with benzyl chloride to give a compound of the formula:

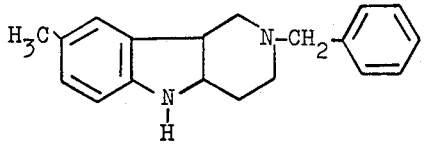

[V], reacting the resulting compound [V] with formic acid and formalin or with ethyl iodide, by which the hydrogen attached to nitrogen atom at 5 position of the compound [V] is replaced by methyl or ethyl group, respectively, and then subjecting the resulting compound to hydrogenolysis in the presence of a palladium on carbon catalyst.

Process (2):

The compounds [I] and their pharmaceutically acceptable acid addition salts may be prepared by reacting a compound of the formula:

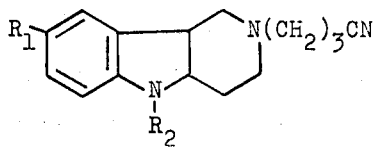

[VI]

wherein R₁ and R₂ are as defined in the first instance, with a Grignard reagent of the formula:

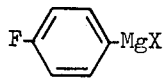

[VII]

wherein X is bromine or iodine, and then hydrolyzing the resulting intermediate.

The Grignard reaction of the Process (2) may be carried out by heating a mixture of the compound [VI] and the Grignard reagent [VII] in an inert solvent, such as ethers (e.g. diethyl ether, tetrahydrofuran or dioxane), which is preferably anhydrous. When the compound [VI] wherein R₂ is hydrogen is used, the Grignard reagent [VII] is preferably used in a double or more amount of the theoretical amount. Suitable reaction temperature may be 30° to 100°C.

The hydrolysis in the above Process (2) may usually be carried out by treating the resulting intermediate with a mineral acid (e.g. dilute hydrochloric acid or dilute sulfuric acid). Suitable reaction temperature therein may be 20° to 90°C, and the reaction time may usually be 10 minutes to one hour.

The starting material [VI] may be prepared by reacting the compound [II] with γ-bromobutyronitrile in an inert solvent (e.g. benzene or toluene) in the presence of the basic condensing agent (e.g. triethylamine). Besides, the Grignard reagent [VII] may be prepared by a conventional process, for instance, by adding a p-fluorohalobenzene to a dispersion of magnesium metal in an inert solvent, such as dry diethyl ether, dry tetrahydrofuran or dry dioxane, wherein the reaction can proceed more smoothly by heating the mixture in the presence of a reaction promotor, such as iodine or methyl iodide.

Process (3):

The compounds [I] and their pharmaceutically acceptable acid addition salts may be prepared by reacting a compound of the formula:

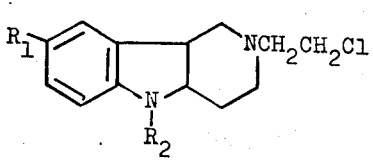

[VIII]

wherein R₁ and R₂ are as defined in the first instance, or its salt with a compound of the formula:

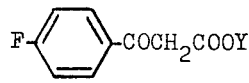

[IX]

wherein Y is a lower alkyl, in the presence of a basic condensing agent to give a compound of the formula:

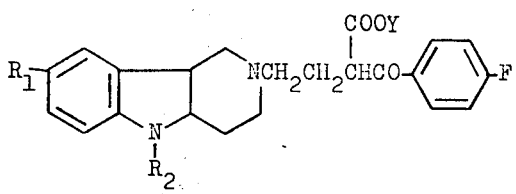

[X]

wherein R₁ and R₂ are as defined in the first instance and Y is as defined above, and then reacting the resulting compound [X] with a base or an acid.

The first step in the above Process (3) may be carried out by heating a mixture of the compound [IX] and an equimolar or slightly excess amount of the compound [VIII] in an inert solvent in the presence of a basic condensing agent. Suitable inert solvent may be benzene, toluene, xylene, dioxane, or the like, which is preferably anhydrous. Suitable basic condensing agent may be sodium metal, sodium hydride, sodium amide, or the like, which is preferably used in an equimolar or slightly excess amount to the compound [IX]. The reaction temperature may usually be 50° to 130°C, and the reaction time may usually be 5 to 15 hours. The reaction is preferably carried out by pre-heating a mixture of the compound [IX] and the basic condensing agent, adding the compound [VIII] to the resulting mixture and then heating the mixture.

The compound [X] thus obtained may be used in the subsequent step without isolation or purification.

The second step in the above Process (3) may be carried out by heating the compound [X] obtained above in a solvent in the presence of a base or an acid. Suitable solvent used therein may be a lower alkanol (e.g. methanol, ethanol or isopropanol), water or a mixture thereof. Suitable base may be an alkali metal hydroxide (e.g. sodium hydroxide or potassium hydroxide), and suitable acid may be a mineral acid (e.g. hydrochloric acid or sulfuric acid). The reaction temperature may usually be 50° to 100°C, and the reaction time may usually be 10 minutes to 5 hours.

The starting material [VIII] may be prepared by reacting the compound [II] with ethylene bromohydrin in an inert solvent (e.g. methyl ethyl ketone or toluene) in the presence of a basic condensing agent (e.g. potassium carbonate or triethylamine) to give a 2-(β-hydroxyethyl) compound, and then reacting the resulting compound with thionyl chloride.

Process (4):

The compounds [I] and their pharmaceutically acceptable acid addition salts may be prepared by reacting a compound of the formula:

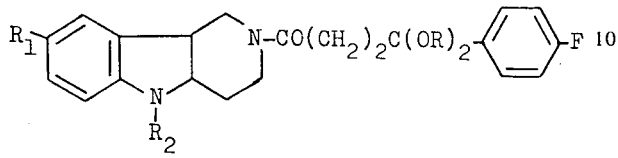

[XI]

wherein $R_1$ and $R_2$ are as defined in the first instance, and each R is a lower alkyl or both R combine with each other to form an alkylene group, with a reducing agent to give a compound of the formula:

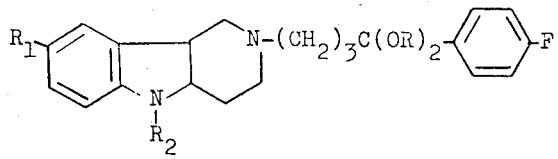

[XII]

wherein $R_1$ and $R_2$ are as defined in the first instance, and R is as defined above, and then hydrolyzing the resulting compound [XII].

The reduction reaction of the first step in the above Process (4) may be carried out by reacting the compound [XI] with a slightly excess amount (to the theoretical amount) of the reducing agent in an inert solvent, such as diethyl ether, tetrahydrofuran, 1,2-dimethoxyethane, dioxane or diglyme. Suitable reducing agent used therein may be an alkali metal aluminum hydride (e.g. lithium aluminum hydride or sodium aluminum hydride) or sodium bis(2-methoxyethoxy)aluminum hydride, but the preferred one is lithium aluminum hydride. The reaction temperature may usually be 30° to 100°C, preferably 35° to 80°C.

The compound [XII] thus obtained may be used in the subsequent hydrolysis step without isolation or purification.

The hydrolysis of the second step in the above Process (4) may be carried out by reacting the compound [XII] obtained above with a mineral acid (e.g. dilute hydrochloric acid or dilute sulfuric acid) at 20° to 80°C for 5 to 30 minutes.

The starting material [XI] may be prepared by reacting the mixed acid anhydride prepared from β-(p-fluorobenzoyl)-propionic acid and alkyl chloroformate (e.g. ethyl chloroformate) with the compound [II] to give a compound of the formula:

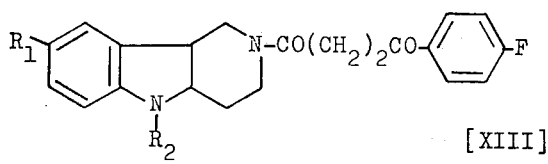

[XIII]

wherein $R_1$ and $R_2$ are as defined in the first instance, and heating the resulting compound [XIII] with an alkanol (e.g. ethylene glycol) in a solvent (e.g. benzene or toluene) in the presence of an excess amount of p-toluenesulfonic acid.

Process (5):

The compounds [I] wherein $R_1$ is methyl and $R_2$ is methyl or ethyl and their pharmaceutically acceptable acid addition salts may also be prepared by reacting a compound of the formula:

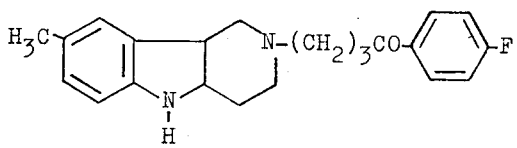

[I']

or its salt with a methylating agent or an ethylating agent, respectively.

The reaction of the above Process (5) may be carried out by heating a mixture of the compound [I'] and an equimolar or slightly excess amount of the methylating agent or ethylating agent in the presence or absence of an inert solvent. The methylating and ethylating agent may be anyone of the conventional one, and may be, for instance, methyl (or ethyl) iodide, dimethyl (or diethyl) sulfate, methyl (or ethyl) p-toluenesulfonate, methyl (or ethyl) benzenesulfonate, formic acid-formalin (for methylation), or the like. The inert solvent used in the reaction may vary with the kinds of the methylating or ethylating agents, but may be, for instance, an aromatic hydrocarbon (e.g. toluene or xylene), a lower alkanol (e.g. isopropanol or butanol), a lower alkanone (e.g. acetone, methyl ethyl ketone or 4-methyl-2-pentanone), diethyl ether, or the like.

The reaction of the above Process (5) may optionally be carried out in the presence of a basic condensing agent, such as an alkali metal carbonate (e.g. potassium carbonate or sodium carbonate), a tertiary amine (e.g. triethylamine), or sodium amide. Further, the reaction temperature may vary with the kinds of the methylating or ethylating agents, but may usually be in a range of room temperature to 160°C.

According to the above processes, the compounds of the present invention may be obtained in a form of a salt or as a free base, which depends on the kinds of the starting materials, the conditions of the reaction, or the like. When the compound is obtained in a form of a salt, it can be easily converted into a free base by a conventional method, for instance, by treating the salt with a base such as an alkali metal hydroxide (e.g. potassium hydroxide or sodium hydroxide) or with an ion-exchange resin. On the other hand, when the compound is obtained as a free base, it can be easily converted into a pharmaceutically acceptable acid addition salt thereof by a conventional method, for instance, by treating the free base with a pharmaceutically acceptable inorganic or organic acid, such as an inorganic acid (e.g. hydrochloric acid, hydrobromic acid, hydroiodic acid, sulfuric acid, nitric acid or phosphoric acid) or an organic acid (e.g. acetic acid, citric acid, maleic acid, oxalic acid, fumaric acid, succinic acid, lactic acid, malic acid, tartaric acid, benzoic acid or methanesulfonic acid).

The preparation of the compounds of the present invention and the compositions thereof are illustrated by the following Examples but not limited thereto. In the Examples, all melting points were determined on a Yanagimoto Micromelting point Apparatus (hot stage) and are uncorrected.

EXAMPLE 1

Preparation of
8-methyl-2-[γ-(p-fluorobenzoyl)propyl]-2,3,4,4a,5,9b-hexahydro-1H-pyrido[4,3-b]indole 1. To toluene (60 ml) are added 8-methyl-2,3,4,4a,5,9b-hexahydro-1H-pyrido[4,3-b]indole (2.5 g), γ-(p-fluorobenzoyl)propyl chloride (2.7 g), triethylamine (1.7 g) and potassium iodide (0.4 g), and the mixture is refluxed for 25 hours. After cooling, the reaction mixture is washed with water, dried over anhydrous sodium sulfate and concentrated under reduced pressure to give a crude product as an oily substance.

The crude product is dissolved in ethanol and thereto is added a 35 % ethanolic hydrogen chloride. The mixture is concentrated under reduced pressure and the resulting residue is recrystallized from aqueous ethanol to give the dihydrochloride of the titled compound (3.0 g), m.p. 185° – 188°C.

The titled compound is treated with an equimolar amount of citric acid in a conventional manner to give the citrate of the compound, m.p. 154° – 158°C (recrystallized from ethanol-acetone).

Similarly, the fumarate of the compound is prepared, m.p. 144° – 147°C (recrystallized from ethyl acetate).

2. To methyl ethyl ketone (150 ml) are added 8-methyl-2,3,4,4a,5,9b-hexahydro-1H-pyrido[4,3-b]indole (9.4 g), γ-(p-fluorobenzoyl)propyl chloride (13.0 g), potassium carbonate (14.0 g) and potassium iodide (12.5 g), and the mixture is refluxed with stirring for 15 hours. After cooling, the insoluble materials are filtered off and the filtrate is concentrated. The resulting residue is dissolved in a dilute hydrochloric acid and the solution is washed with ethyl acetate and concentrated. To the residue is added ethanol, and the precipitated crystals are separated by filtration and recrystallized from aqueous ethanol to give the dihydrochloride of the titled compound (14.0 g), m.p. 185° – 188°C.

EXAMPLE 2

Preparation of
8-ethyl-2-[γ-(p-fluorobenzoyl)propyl]-2,3,4,4a,5,9b-hexahydro-1H-pyrido[4,3-b]indole To methyl ethyl ketone (120 ml) are added 8-ethyl-2,3,4,4a,5,9b-hexahydro-1H-pyrido[4,3-b]indole (9 g), γ-(p-fluorobenzoyl)propyl chloride (12 g), potassium carbonate (12 g) and potassium iodide (11 g), and the mixture is refluxed with stirring for 9 hours. After cooling, the insoluble materials are filtered off and the filtrate is concentrated. The resulting residue is dissolved in a dilute hydrochloric acid and the solution is washed with benzene. The dilute hydrochloric acid layer is made alkaline with aqueous ammonia and extracted with benzene. The benzene layer is dried over anhydrous sodium sulfate and concentrated. The resulting residue is treated with ethanolic hydrochloric acid in the same manner as described in Example 1 (1) to give the dihydrochloride of the titled compound (12 g), m.p. 192° – 195°C (recrystallized from aqueous ethanol).

EXAMPLE 3

In the same manner as described in Examples 1 and 2, the following compounds are prepared.
5,8-Dimethyl-2-[γ-(p-fluorobenzoyl)propyl]-2,3,4,4a,5,9b-hexahydro-1H-pyrido[4,3-b]indole dihydrochloride, m.p. 140° – 145°C (recrystallized from aqueous ethanol)
5-Ethyl-8-methyl-2-[γ-(p-fluorobenzoyl)propyl]-2,3,4,4a,5,9b-hexahydro-1H-pyrido[4,3-b]indole dihydrochloride, m.p. 150° – 153°C (recrystallized from ethanol)

EXAMPLE 4

Preparation of
5,8-dimethyl-2-[γ-(p-fluorobenzoyl)-propyl]-2,3,4,4a,5,9b-hexahydro-1H-pyrido[4,3-b]indole To magnesium (0.49 g) is added dry ether (15 ml) and thereto is gradually added with stirring a solution of p-fluorobromobenzene (3.56 g) in dry ether (5 ml) at a rate sufficient to maintain the reflux. After the addition, the mixture is further refluxed for one hour. To the mixture is added a solution of 2-(γ-cyanopropyl)-5,8-dimethyl-2,3,4,4a,5,9b-hexahydro-1H-pyrido[4,3-b]indole (3.3.g) in dry ether (15 ml) at such a rate that the reflux temperature is maintained. After the addition, the mixture is refluxed for 10 hours and thereto a dilute hydrochloric acid is added under cooling. The mixture is stirred for a while and then the dilute hydrochloric acid layer is separated. The dilute hydrochloric acid layer is heated at 70°C for 1 hour, and then cooled. The dilute hydrochloric acid layer is made alkaline with aqueous ammonia and extracted with benzene. The benzene layer is dried over anhydrous sodium sulfate and concentrated to give a crude product as an oily substance. The crude product is treated with ethanolic hydrogen chloride in the same manner as described in Example 1 (1) to give the dihydrochloride of the titled compound (2.5 g), m.p. 140° – 145°C (recrystallized from aqueous ethanol).

EXAMPLE 5

Preparation of
8-methyl-2-[γ-(p-fluorobenzoyl)propyl]-2,3,4,4a,5,9b-hexahydro-1H-pyrido[4,3-b]indole To magnesium (0.53 g) is added dry ether (15 ml) and thereto is gradually added with stirring a solution of p-fluorobromebenzene (3.9 g) in dry ether (10 ml) at a rate sufficient to maintain the reflux. After the addition, the mixture is further refluxed for one hour. To the mixture is added in portions a solution of 2-(γ-cyanopropyl)-8-methyl-2,3,4,4a,5,9b-hexahydro-1H-pyrido[4,3-b]indole (2.6 g) in dry ether (100 ml) and then the mixture is refluxed for 13 hours. To the reaction mixture is added in portions aqueous ammonium chloride under cooling, and the mixture is stirred for a while and then the ether layer is separated. The ether layer is extracted with a dilute hydrochloric acid and the extract is heated at 70°C for one hour. After cooling, the extract is made alkaline with aqueous sodium hydroxide and extracted with benzene. The benzene layer is dried over anhydrous sodium sulfate and distilled to remove benzene. The resulting residue is subjected to a column chromatography of silica gel (30 g) and eluted with chloroform-ethanol (30 : 1 by volume). The eluates are collected and then treated with ethanolic hydrogen chloride in the same manner as described in Example 1 (1) to give the dihydrochloride of the titled compound (1.4 g), m.p. 185°– 188°C (recrystallized from aqueous ethanol).

EXAMPLE 6

In the same manner as described in Examples 4 and 5, the following compounds are prepared.

8-Ethyl-2-[γ-(p-fluorobenzoyl)propyl]-2,3,4,4a,5,9b-hexahydro-1H-pyrido[4,3-b]indole dihydrochloride, m.p. 192°– 195°C (recrystallized from aqueous ethanol)

5-Ethyl-8-methyl-2-[γ-(p-fluorobenzoyl)propyl]-2,3,4,4a,5,9b-hexahydro-1H-pyrido[4,3-b]indole dihydrochloride, m.p. 150° – 153°C (recrystallized from ethanol)

EXAMPLE 7

Preparation of 8-methyl-2-[γ-(p-fluorobenzoyl)propyl]-2,3,4,4a,5,9b-hexahydro-1H-pyrido[4,3-b]indole a. To a solution of 2-(β-hydroxyethyl)-8-methyl-2,3,4,4a,5,9b-hexahydro-1H-pyrido[4,3-b]indole (2.3 g) in benzene (50 ml) is added in portions a solution of thionyl chloride (3.5 g) in benzene (8 ml), and the mixture is stirred at room temperature for 3.5 hours. After cooling, to the reaction mixture is added water. The aqueous layer is made alkaline with potassium carbonate and extracted with benzene. The benzene layer is dried over anhydrous sodium sulfate and concentrated to give crude 2-(β-chloroethyl)-8-methyl-2,3,4,4a,5,9b-hexahydro-1H-pyride[4,3-b]indole (1.8 g) as an oily substance.

b. A mixture of ethyl (p-fluorobenzoyl)acetate (2.0 g) and sodium (0.29 g) in dry xylene (50 ml) is heated with stirring at 120°– 130°C for 3 hours. Under cooling to lower than 10°C, to the mixture is added in portions a solution of 2-chloroethyl compound (1.8 g) obtained in the above (a) in dry xylene (10 ml), and the mixture is refluxed for 8 hours. After cooling, the reaction mixture is poured into water, and then the xylene layer is separated. The aqueous layer is extracted with benzene. The benzene layer is combined with the above xylene layer, and the organic layer is distilled to remove the solvents. The resulting residue is added to a solution of sodium hydroxide (4 g) in a mixture of methanol (100 ml) and water (4 ml). The mixture is refluxed for 30 minutes and then concentrated. To the residue is added water and the mixture is extracted with benzene. The benzene layer is dried over anhydrous sodium sulfate and concentrated. The resulting residue is subjected to a column chromatography of silica gel (15 g) and eluted with chloroform-ethanol (50 : 1 by volume). The eluates are collected and then treated with ethanolic hydrogen chloride in the same manner as described in Example 1 (1) to give the dihydrochloride of the titled compound (1.1 g), m.p. 185°– 188°C (recrystallized from aqueous ethanol).

EXAMPLE 8

Preparation of 5,8-dimethyl-2-[γ-(p-fluorobenzoyl)propyl]-2,3,4,4a,5,9b-hexahydro-1H-pyrido[4,3-b]indole a. In the same manner as described in Example 7, 2-(β-hydroxyethyl)-5,8-dimethyl-2,3,4,4a,5,9b-hexahydro-1H-pyrido-[4,3-b]indole (3.5 g) is reacted with thionyl chloride (5.0 g) to give 2-(β-chloroethyl)-5,8-dimethyl-2,3,4,4a,5,9b-hexahydro-1H-pyrido[4,3-b]indole (2.9 g) as an oily substance.

b. To a solution of ethyl (p-fluorobenzoyl)acetate (3.0 g) in dry toluene (50 ml) is added a 50 % dispersion of sodium hydride (0.4 g) in mineral oil. The mixture is heated with stirring at 60°C for 1 hour and thereto is added in portions a solution of 2-chloroethyl compound (2.9 g) obtained in the above (a) in dry toluene (15 ml), and the mixture is refluxed for 6 hours. After cooling, the insoluble materials are filtered off and the filtrate is concentrated. The resulting residue is dissolved in methanol (100 ml) and thereto are added water (5 ml) and sodium hydroxide (5 g). The mixture is refluxed for 30 minutes and then concentrated. To the residue is added water, and the mixture is extracted with benzene. The benzene layer is dried over anhydrous sodium sulfate and distilled to remove benzene. The resulting residue is subjected to a column chromatography of silica gel (35 g) and eluted with chloroform. The eluates are collected and treated with ethanolic hydrogen chloride in the same manner as described in Example 1 (1) to give the dihydrochloride of the titled compound (1.9 g), m.p. 140° – 145°C (recrystallized from aqueous ethanol).

EXAMPLE 9

In the same manner as described in Examples 7 and 8, the following compounds are prepared.

8-Ethyl-2-[γ-(p-fluorobenzoyl)propyl]-2,3,4,4a,5,9b-hexahydro-1H-pyrido[4,3-b]indole dihydrochloride, m.p. 192°– 195°C (recrystallized from aqueous ethanol)

5-Ethyl-8-methyl-2-[γ-(p-fluorobenzoyl)propyl]-2,3,4,4a,5,9b-hexahydro-1H-pyrido[4,3-b]indole dihydrochloride, m.p. 150° – 153°C (recrystallized from ethanol)

EXAMPLE 10

Preparation of 8-ethyl-2-[γ-(p-fluorobenzoyl)propyl]-2,3,4,4a,5,9b-hexahydro-1H-pyrido[4,3-b]indole a. To toluene (120 ml) are added 2-[β-(p-fluorobenzoyl)propionyl]-8-ethyl-2,3,4,4a,5,9b-hexahydro-1H-pyrido-[4,3-b]indole (3.5 g), p-toluenesulfonic acid (2.2 g) and ethylene glycol (60 ml), and the mixture is refluxed with stirring for 6 hours while separating the isolated water. After cooling, the under layer is separated and thereto is added water. The mixture is made alkaline with aqueous ammonia and extracted with ether. The ether layer is dried over anhydrous sodium sulfate and concentrated to give 2-[γ,γ-ethylenedioxy-γ-(p-fluorophenyl)butyryl]-8-ethyl-2,3,4,4a,5,9b-hexahydro-1H-pyrido[4,3-b]indole, m.p. 120° – 123°C (recrystallized from ether).

b. To a suspension of lithium aluminum hydride (0.45 g) in dry ether (50 ml) is added dropwise a solution of the ketal compound (3.2 g) obtained in the above (a) in dry ether (15 ml). The mixture is refluxed with stirring for 3 hours, and thereto is added water (2 ml) under cooling. The resulting insoluble materials are filtered off and the filtrate is extracted with a dilute hydrochloric acid. The dilute hydrochloric acid layer is made alkaline with aqueous ammonia and extracted with ether. The ether layer is dried over anhydrous sodium sulfate and concentrated to give a crude product as an oily substance. The crude product is treated with ethanolic hydrogen chloride in the same manner as described in Example 1 (1) to give the dihydrochloride of the titled compound (2.4 g), m.p. 192° – 195°C (recrystallized from aqueous ethanol).

EXAMPLE 11

Preparation of 8-methyl-2-[γ-(p-fluorobenzoyl)propyl]-2,3,4,4a,5,9b-hexahydro-1H-pyrido[4,3-b]indole a. In the same manner as described in Example 10 (a), 2-[β-(p-fluorobenzoyl)propionyl]-8-methyl-2,3,4,4a,5,9b-hexahydro-1H-pyrido[4,3-b]indole (7.0 g), p-toluenesulfonic acid (4.8 g) and ethylene glycol (80 ml) are treated to give 2-[γ,γ-ethylenedioxy-γ-(p-fluorophenyl)butyryl]-8-methyl-2,3,4,4a,5,9b-hexahydro-1H-pyrido[4,3-b]indole (6.5 g), m.p. 136° – 138°C (recrystallized from acetone-ether).

b. To a suspension of lithium aluminum hydride (1.0 g) in dry tetrahydrofuran (150 ml) is added in portions with stirring a solution of the ketal compound (6.5 g) obtained in the above (a) in dry tetrahydrofuran (20 ml). The mixture is refluxed for 3 hours and thereto is added water (4 ml) under cooling. The resulting insoluble materials are filtered off and the filtrate is concentrated. The resulting residue is dissolved in a dilute hydrochloric acid and the mixture is heated at 50°C for 20 minutes. After cooling, the mixture is made alkaline with aqueous ammonia and extracted with ether. The ether layer is dried over anhydrous sodium sulfate and distilled to remove ether. The resulting residue is treated with ethanolic hydrogen chloride in the same manner as described in Example 1 (1) to give the dihydrochloride of the titled compound (5.2 g), m.p. 185° – 188°C (recyrstallized from aqueous ethanol).

EXAMPLE 12

In the same manner as described in Examples 10 and 11, the following compounds are prepared.
5,8-Dimethyl-2-[γ-(p-fluorobenzoyl)propyl]-2,3,4,4a,5,9b-hexahydro-1H-pyrido[4,3-b]indole dihydrochloride, m.p. 140° – 145°C (recrystallized from aqueous ethanol)
5-Ethyl-8-methyl-2-[γ-(p-fluorobenzoyl)propyl]-2,3,4,4a,5,9b-hexahydro-1H-pyrido[4,3-b]indole dihydrochloride, m.p. 150° – 153°C (recrystallized from ethanol)

EXAMPLE 13

Preparation of 5,8-dimethyl-2-[γ-(p-fluorobenzoyl)propyl]-2,3,4,4a,5,9b-hexahydro-1H-pyrido[4,3-b]indole A mixture of 8-methyl-2-[γ-(p-fluorobenzoyl)propyl]-2,3,4,4a,5,9b-hexahydro-1H-pyrido[4,3-b]indole (7.5 g), formic acid (2.7 g) and formalin (2.2 g) is refluxed for 3 hours. After cooling, to the reaction mixture is added water, and the mixture is made alkaline with aqueous sodium hydroxide and extracted with benzene. The benzene layer is dried over anhydrous sodium sulfate and concentrated. The resulting residue is treated with ethanolic hydrogen chloride in the same manner as described in Example 1 (1) to give the dihydrochloride of the titled compound (4.1 g), m.p. 140° – 145°C (recrystallized from aqueous ethanol).

EXAMPLE 14

Preparation of 5-ethyl-8-methyl-2-[γ-(p-fluorobenzoyl)-propyl]-2,3,4,4a,5,9b-hexahydro-1H-pyrido[4,3-b]indole To methyl ethyl ketone (60 ml) are added 8-methyl-2-[γ-(p-fluorobenzoyl)propyl]-2,3,4,4a,5,9b-hexahydro-1H-pyrido-[4,3-b]indole (6.6 g), ethyl iodide (3.8 g) and potassium carbonate (5.3 g) and the mixture is refluxed with stirring for 20 hours. After cooling, the insoluble materials are filtered off and the filtrate is concentrated. To the resulting residue is added water and the mixture is extracted with benzene. The benzene layer is dried over anhydrous sodium sulfate and distilled to remove benzene. The resulting residue is treated with ethanolic hydrogen chloride in the same manner as described in Example 1 (1) to give the dihydrochloride of the titled compound (5.2 g), m.p. 150° – 153°C (recrystallized from ethanol).

The starting materials used in the above Examples are prepared as follows:

Reference Example 1

Preparation of 8-methyl-2,3,4,5-tetrahydro-1H-pyrido-[4,3-b]indole

To a mixture of concentrated hydrochloric acid (13 ml) and isopropyl alcohol (90 ml) are added p-tolylhydrazine hydrochloride (8.0 g) and 4,4-ethylenedioxypiperidine (7.0 g) and the mixture is refluxed for 70 minutes. After cooling, the precipitated crystals are separated by filtration and recrystallized from 70 % methanol to give the hydrochloride of the titled compound (10.0 g), m.p. 273° – 275°C.

Reference Example 2

In the same manner as described in Reference Example 1, the following compound is prepared.
8-Ethyl-2,3,4,5-tetrahydro-1H-pyrido[4,3-b]indole hydrochloride, m.p. 255° – 258°C (recrystallized from aqueous ethanol)

Reference Example 3

Preparation of 8-methyl-2,3,4,4a,5,9b-hexahydro-1H-pyrido[4,3-b]indole

To a mixture of water (50 ml) and 42 % borofluoric acid (18 ml) is added 8-methyl-2,3,4,5-tetrahydro-1H-pyrido[4,3-b]indole hydrochloride (5.7 g), and the mixture is subjected to a catalytic reduction under heating in the presence of platinum dioxide (0.2 g). When hydrogen (820 ml) is absorbed, the catalyst is filtered off and the filtrate is made alkaline with aqueous ammonia, salted out with potassium carbonate and extracted with benzene. The benzene layer is washed with water, dried over anhydrous sodium sulfate and concentrated to give the titled compound (4.2 g), m.p. 73° – 75°C.

The compound thus obtained is reacted with two molar amount of oxalic acid in a conventional manner to give the dioxalate of the compound, m.p. 188° – 189°C (recrystallized from methanol).

Reference Example 4

In the same manner as described in Reference Example 3, the following compound is prepared.
8-Ethyl-2,3,4,4a,5,9b-hexahydro-1H-pyrido[4,3-b]-indole, m.p. 82° – 85°C (recrystallized from ether-petroleum ether)

Reference Example 5

Preparation of 2-benzyl-8-methyl-2,3,4,4a,5,9b-hexahydro-1H-pyrido[4,3-b]indole

To toluene (100 ml) are added 8-methyl-2,3,4,4a,5,9b-hexahydro-1H-pyrido[4,3-b]indole (10 g), benzyl chloride (7.4 g) and triethylamine (8.1 g), and the mixture is refluxed for 15 hours. After cooling, the reaction mixture is washed with water, dried over anhydrous sodium sulfate and distilled under reduced pressure to remove toluene. The resulting residue is treated with ethanolic hydrogen chloride in the same manner as described in Example 1 (1) to give the dihydrochloride of the titled compound (11.0 g), m.p. 179° – 182°C (recrystallized from ethanol).

Reference Example 6

Preparation of 5,8-dimethyl-2,3,4,4a,5,9b-hexahydro-1H-pyrido[4,3-b]indole

To 2-benzyl-8-methyl-2,3,4,4a,5,9b-hexahydro-1H-pyrido[4,3-b]indole (6.0 g) are added formic acid (2.7 g) and formalin (2.1 g), and the mixture is refluxed for 3 hours. After cooling, the reaction mixture is made alkaline with aqueous sodium hydroxide and extracted with benzene. The benzene layer is dried over anhydrous sodium sulfate and distilled to remove benzene. The resulting oily substance is subjected to a column chromatography of silica gel (50 g) and eluted with chloroform. The eluates are collected to give 2-benzyl-5,8-dimethyl-2,3,4,4a,5,9-b-hexahydro-1H-pyrido[4,3-b]indole (4.0 g) as an oily substance. The oily substance is dissolved in 70 % methanol (90 ml) and the mixture is subjected to a catalytic reduction in the presence of 10 % palladium on carbon (0.5 g) until hydrogen (350 ml) is absorbed. After filtering off the catalyst, the filtrate is concentrated and the resulting residue is subjected to a column chromatography of silica gel (20 g) and eluted with chloroform and then with methanol. The eluates with methanol are collected to give the titled compound as an oily substance. This compound thus obtained is reacted with an equimolar amount of maleic acid in a conventional manner to give the maleate (2.5 g) of the compound, m.p. 169° – 171°C (recrystallized from ethanol-ethyl acetate).

Reference Example 7

The above Reference Example 6 is repeated excepting that ethyl iodide is used instead of formic acid and formalin to give 5-ethyl-8-methyl-2,3,4,4a,5,9b-hexahydro-1H-pyrido-[4,3-b]indole as an oily substance. This compound thus obtained is reacted with an equimolar amount of maleic acid in a conventional manner to give the maleate of the compound, m.p. 160° – 162°C (recrystallized from ethanol-ethyl acetate).

Reference Example 8

Preparation of 2-(γ-cyanopropyl)-8-methyl-2,3,4,4a,5,9b-hexahydro-1H-pyrido[4,3-b]indole In toluene (60 ml) are dissolved 8-methyl-2,3,4,4a,5,9b-hexahydro-1H-pyrido[4,3-b]indole (5.7 g), γ-bromobutyronitrile (4.5 g) and triethylamine (4.6 g), and the mixture is refluxed for 5 hours. After cooling, the reaction mixture is washed with water, dried over anhydrous sodium sulfate and distilled under reduced pressure to remove toluene. The resulting residue is treated with ethanolic hydrogen chloride in the same manner as described in Example 1 (1) to give the dihydrochloride of the titled compound (5.5 g), m.p. 160° – 165°C (recrystallized from aqueous ethanol).

Reference Example 9

In the same manner as described in Reference Example 8, the following compounds are prepared.
2-(γ-Cyanopropyl)-8-ethyl-2,3,4,4a,5,9b-hexahydro-1H-pyrido[4,3-b]indole dipicrate, m.p. 108° – 112°C (recrystallized from acetone-ethanol)
2-(γ-Cyanopropyl)-5,8-dimethyl-2,3,4,4a,5,9b-hexahydro-1H-pyrido[4,3-b]indole maleate, m.p. 162° – 164°C (recrystallized from ethanol)
2-(γ-Cyanopropyl)-5-ethyl-8-methyl-2,3,4,4a,5,9b-hexahydro-1H-pyrido[4,3-b]indole maleate, m.p. 124° – 126°C (recrystallized from ethyl acetate)

Reference Example 10

Preparation of 2-(β-hydroxyethyl)-8-methyl-2,3,4,4a,5,9b-hexahydro-1H-pyrido[4,3-b]indole A mixture of 8-methyl-2,3,4,4a,5,9b-hexahydro-1H-pyrido[4,3-b]indole (10.0 g), ethylene bromohydrin (8.0 g) and potassium carbonate (14.6 g) in methyl ethyl ketone (80 ml) is refluxed with stirring for 16 hours. The insoluble materials are filtered off and the filtrate is concentrated under reduced pressure. The resulting residue is dissolved in a dilute hydrochloric acid. The dilute hydrochloric acid layer is separated, washed with benzene, made alkaline with aqueous sodium hydroxide and then extracted with benzene. The benzene layer is dried over anhydrous sodium sulfate and concentrated to give a crude product as an oily substance. The crude product is treated in the same manner as described in Example 1 (1) to give the dihydrochloride of the titled compound (7.8 g), m.p. 182° –185°C (recrystallized from aqueous ethanol).

Reference Example 11

In the same manner as described in Reference Example 10, the following compounds are prepared.
2-(β-Hydroxyethyl)-8-ethyl-2,3,4,4a,5,9b-hexahydro-1H-pyrido[4,3-b]indole dipicrate, m.p. 131° – 135°C (recrystallized from acetone-ethanol)
2-(β-Hydroxyethyl)-5,8-dimethyl-2,3,4,4a,5,9b-hexahydro-1H-pyrido[4,3-b]indole dihydrochloride, m.p. 148° – 152°C (recrystallized from ethanol)
2-(β-Hydroxyethyl)-5-ethyl-8-methyl-2,3,4,4a,5,9b-hexahydro-1H-pyrido[4,3-b]indole oxalate, m.p. 175° – 177°C (recrystallized from ethanol)

Reference Example 12

Preparation of
2-[β-(p-fluorobenzoyl)propionyl]-8-ethyl-
2,3,4,4a,5,9b-hexahydro-1H-pyrido[4,3-b]indole To a solution of β-(p-fluorobenzyl)propionic acid (3.0 g) and triethylamine (1.7 g) in dry tetrahydrofuran (90 ml) is added dropwise ethyl chloroformate (1.8 g) under maintaining the temperature of the system at 0° – 2°C. The mixture is stirred at the same temperature for 30 minutes. The mixture is added in portions of 8-ethyl-2,3,4,4a,5,9b-hexahydro-1H-pyrido[4,3-b]indole (3.3 g) in dry tetrahydrofuran (50 ml) so that the temperature in the system is maintained at 0° – 2°C. After the addition, the mixture is stirred at room temperature for one hour and then refluxed for one hour. After cooling, the precipitated crystals are filtered off and the filtrate is concentrated. The resulting residue is recrystallized from ethanol to give the titled compound (4.2 g), m.p. 120° – 124°C.

Reference Example 13

In the same manner as described in Reference Example 12, the following compounds are prepared.
2-[β-(p-Fluorobenzoyl)propionyl]-8-methyl-
2,3,4,4a,5,9b-hexahydro-1H-pyrido[4,3-b]indole,
m.p. 106° – 109°C (recrystallized from ethanol)
2-[β-(p-Fluorobenzoyl)propionyl]-5,8-dimethyl-
2,3,4,4a,5,9b-hexahydro-1H-pyrido[4,3-b]indole,
oily substance
2-[β-(p-Fluorobenzoyl)propionyl]-5-ethyl-8-methyl-
2,3,4,4a,5,9b-hexahydro-1H-pyrido[4,3-b]indole,
oily substance

Example 15

| | |
|---|---|
| 8-Methyl-2-[γ-(p-fluorobenzoyl)propyl]-2,3,4,4a,5,9b-hexahydro-1H-pyrido[4,3-b]-indole dihydrochloride | 25 g |
| Lactose | 53 g |
| Starch | 25 g |
| Microcrystalline cellulose | 90 g |
| Light anhydrous silicic acid | 2 g |
| Hardened oil | 3 g |
| Magnesium stearate | 2 g |

The above components are blended, granulated and made into tablets by the conventional method. The 1000 tablets each weighing 200 mg are formed.

Example 16

| | |
|---|---|
| 8-Methyl-2-[γ-(p-fluorobenzoyl)propyl]-2,3,4,4a,5,9b-hexahydro-1H-pyrido[4,3-b]-indole dihydrochloride | 100 g |
| Starch | 895 g |
| Light anhydrous silicic acid | 4 g |
| Magnesium stearate | 1 g |

The above components are blended and made into powder by the conventional method.

What is claimed is:

1. A hexahydro-γ-carboline derivative of the formula:

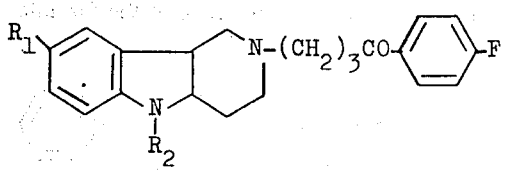

wherein $R_1$ is methyl or ethyl, and $R_2$ is hydrogen, methyl or ethyl, with proviso that when $R_1$ is ethyl, $R_2$ is hydrogen, and its pharmaceutically acceptable acid addition salt.

2. 8-Methyl-2-[γ-(p-fluorobenzoyl)propyl]-2,3,4,4a,5,9b-hexahydro-1H-pyrido[4,3-b]indole and its pharmaceutically acceptable acid addition salt.

3. 5,8-Dimethyl-2-[γ-(p-fluorobenzoyl)propyl]-2,3,4,4a,5,9b-hexahydro-1H-pyrido[4,3-b]indole and its pharmaceutically acceptable acid addition salt.

4. 5-Ethyl-8-methyl-2-[γ-(p-fluorobenzoyl)propyl]-2,3,4,4a,5,9b-hexahydro-1H-pyrido[4,3-b]indole and its pharmacutically acceptable acid addition salt.

5. 8-Ethyl-2-[γ-(p-fluorobenzoyl)propyl]-2,3,4,4a,5,9b-hexahydro-1H-pyrido[4,3-b]indole and its pharmaceutically acceptable acid addition salt.

6. A pharmaceutical composition for the treatment of schizophrenia in humans, comprising as the essential active ingredient a hexahydro-γ-carboline derivative of the formula:

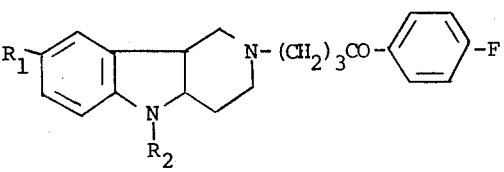

wherein $R_1$ is methyl or ethyl, and $R_2$ is hydrogen, methyl or ethyl, with proviso that when $R_1$ is ethyl, $R_2$ is hydrogen, or a pharmaceutically acceptable acid addition salt thereof in admixture with a pharmaceutically acceptable carrier, the amount of said essential active ingredient being about 25 mg to 1,800 mg in terms of a dosage unit per day.

7. The pharmaceutical composition of claim 6, wherein said active compound is 8-methyl-2-[γ-(p-fluorobenzoyl)-propyl]-2,3,4,4a,5,9b-hexahydro-1H-pyrido[4,3-b]indole or a pharmaceutically acceptable acid addition salt thereof.

8. The pharmaceutical composition of claim 6, wherein said active compound is 5,8-dimethyl-2-[γ-(p-fluorobenzoyl)-propyl]-2,3,4,4a,5,9b-hexahydro-1H-pyrido[4,3-b]indole or a pharmaceutically acceptable acid addition salt thereof.

9. The pharmaceutical composition of claim 6, wherein said active compound is 5-ethyl-8-methyl-2-[γ-(p-fluorobenzoyl)-propyl]-2,3,4,4a,5,9b-hexahydro-1H-pyrido[4,3-b]indole or a pharmaceutically acceptable acid addition salt thereof.

10. The pharmaceutical composition of claim 6, wherein said active compound is 8-ethyl-2-[γ-(p-fluorobenzoyl)-propyl]-2,3,4,4a,5,9b-hexahydro-1H-pyrido[4,3-b]indole or a pharmaceutically acceptable acid addition salt thereof.

11. A method of treating schizophrenia in humans, which comprises administering orally or parenterally to said human an effective amount as a neuroleptic of a hexahydro-γ-carboline derivative of the formula:

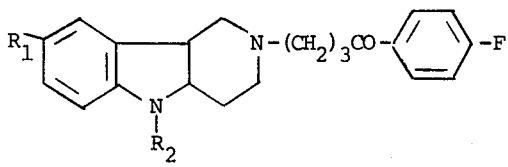

wherein $R_1$ is methyl or ethyl, and $R_2$ is hydrogen, or a pharmaceutically acceptable acid addition salt thereof, either alone or in admixture with a pharmaceutically acceptable carrier.

12. The method of claim 11, wherein said hexahydro-γ-carboline derivative or a pharmaceutically acceptable acid addition salt thereof is orally administered in an amount of about 25 mg to 1,800 mg per day.

13. The method of claim 11, wherein said hexahydro-γ-carboline derivative is 8-methyl-2-[γ-(p-fluorobenzoyl)propyl]-2,3,4,4a,5,9b-hexahydro-1H-pyrido[4,3-b]indole.

14. The method of claim 11, wherein said hexahydro-γ-carboline derivative is 5,8-dimethyl-2-[γ-(p-fluorobenzoyl)propyl]-2,3,4,4a,5,9b-hexahydro-1H-pyrido[4,3-b]indole.

15. The method of claim 11, wherein said hexahydro-γ-carboline derivative is 5-ethyl-8-methyl-2-[γ-(p-fluorobenzoyl)propyl]-2,3,4,4a,5,9b-hexahydro-1H-pyrido[4,3-b]indole.

16. The method of claim 11, wherein said hexahydro-γ-carboline derivative is 8-ethyl-2-[γ-(p-fluorobenzoyl)propyl]-2,3,4,4a,5,9b-hexahydro-1H-pyrido[4,3-b]indole.

* * * * *